DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JULY 18, 1972

900 O.G. 816

T900,001

AMINOMETHYLATING AGENTS AND PROCESSES FOR PREPARING AND USING SAME

Delbert D. Reynolds, Pittsford, and Bernard C. Cossar, Rochester, N.Y. (both of 1669 Lake Ave., Rochester, N.Y. 14615)

Filed Dec. 21, 1970, Ser. No. 100,298
Int. Cl. C07d *87/00*
U.S. Cl. 260—244 R
No Drawing. 51 Pages Specification

Aminomethylating agents are prepared by the reaction of an N,N′,N″-substituted hexahydrotriazine, or a derivative thereof, with hydrogen chloride. The reaction medium is either an inert solvent or an alcohol. When an alcohol is used, the product is an alkoxymethylamine of the structure $$\overset{H_2}{\underset{\oplus}{R}N}-CH_2OR\ X^{\ominus} \text{ or } ROCH_2\overset{H_2}{\underset{\oplus}{N}}-R^1-\overset{H_2}{\underset{\ominus}{N}}-CH_2OR\ X^{\ominus}\ X^{\ominus}$$

wherein R is alkyl or aralkyl, $R^1$ is alkylene or arylene-bisalkylene and X is an anion. When the reaction is conducted in an inert medium, the product is either a chloromethylamine of the formula $RNHCH_2X$ wherein R and X are the same as previously defined, or the trihydrochloride salt of the N,N′,N″-substituted hexahydrotriazine, or a mixture of the two.

Examples of the reaction of the aminomethylating agents with a compound containing an active hydrogen atom to yield Mannich bases containing secondary amine functions are: the aminomethylation of mercaptans to yield compounds of the formula $$\overset{H_2}{\underset{\oplus}{R}N}-CH_2SR^3\ X^{\ominus}$$

wherein R and X are defined above and $R^3$ is an organo group; the aminomethylation of a phenolic compound to yield p-substituted products of the formula

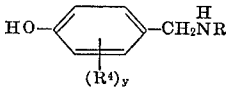

wherein R is the same as previously described, $R^4$ is an alkyl aryl, aralkyl, halogen, dialkylamino, or ester group and $y$ is 0, 1, 2 or 3; the aminomethylation of hydrogen sulfide under acidic conditions to yield products having the general structure $RNHCH_2SCH_2NHR \cdot 2HX$ wherein R and X are the same as previously described, and the aminomethylation of hydroquinone or 2-substituted hydroquinones to yield monobenzoxazine derivatives of the formula

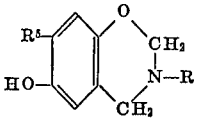

wherein R is as previously described and $R^5$ is an alkyl or aralkyl group. The cleavage of an aminomethylated thioacid containing a secondary amine group to give a bis(secondary aminomethyl)sulfide hydrochloride is also disclosed.